United States Patent [19]

Perry et al.

[11] Patent Number: 4,933,466

[45] Date of Patent: Jun. 12, 1990

[54] PREPARATION OF IMIDES

[75] Inventors: Robert J. Perry; Sam R. Turner, both of Pittsford, N.Y.

[73] Assignee: Eastman Kodak Company, Rochester, N.Y.

[21] Appl. No.: 297,788

[22] Filed: Jan. 17, 1989

[51] Int. Cl.$^5$ ............................................. C07D 209/48
[52] U.S. Cl. ..................................... 548/476; 546/200; 546/201; 546/208; 548/539; 560/97; 560/206; 562/406
[58] Field of Search ...................... 546/200, 201, 208; 548/476, 539; 560/97, 206; 562/406; 260/544 A

[56] References Cited

U.S. PATENT DOCUMENTS 3,988,358  10/1976  Heck ................................... 548/539
4,761,499  8/1988  Epstein ................................. 560/97

Primary Examiner—Anton H. Sutto
Assistant Examiner—D. D. Carr
Attorney, Agent, or Firm—Robert A. Linn

[57] ABSTRACT

Cyclic imides are prepared by reacting carbon monoxide with an ortho dihalide aromatic compound or a cis-1,2-vinyl dihalide and an amine in the presence of palladium catalyst and a base. The process is preferably conducted in the presence of a dipolar aprotic solvent as a liquid reaction medium.

Acyclic imides are prepared by reacting CO with an activated halide and an amide (primary or secondary) in the presence of a Pd catalyst and a base.

2 Claims, No Drawings

PREPARATION OF IMIDES

FIELD OF THE INVENTION

This invention relates to cyclic and acyclic imides and to processes for their preparation. The imides may be monomeric, oligomeric, or polymeric. The processes comprise palladium catalyzed carbonylations. Other catalysts can be used.

RELATED ART

Yoneyama et al, *Macromolecules* (1988) 21, pp. 1908–1911, discloses the synthesis of aromatic polyamides by palladium-catalyzed polycondensation of aromatic dibromides, aromatic diamines, and carbon monoxide.

The literature relating to the carbonylation of aromatic halides, and the formation of amides and other compounds by such a route, is summarized in Heck, R. F., *Palladium Reagents in Organic Syntheses*, Academic Press, New York, N.Y. (1985) pp. 348–359. The preparation of cyclic and acyclic imides by the process of this invention is not suggested by the above references.

Mori et al, *Heterocycles* 13, 329–332 (1979) discloses formation of monomeric cyclic imides and quinolone by the palladium catalyzed carbonylation of aryl and vinyl monobromides having an amine or amide group on a carbon atom adjacent to the carbon substituted with the bromide radical. The reference does not disclose intermolecular condensations and does not disclose the reaction of dibromides or diiodides.

SUMMARY OF THE INVENTION

This invention provides a method for the preparation of cyclic and acyclic imides. The products may be monomeric, oligomeric, or polymeric. The products may also contain amide groups and other functional groups.

The process is illustrated by the following equations depicting the preparation of N-phenylphthalimide from diiodobenzene, aniline, and carbon monoxide. The illustrated process is conducted in the presence of palladium tetrakis(triphenylphosphine) (PdL$_4$), dimethylacetamide (DMAc), and 1,8-diazobicyclo[5,4,0]undec-7-ene (DBU). The DMAc is used as a solvent; the DBU is a base for neutralizing by-product hydrogen halide. One possible mechanism is depicted by the following equations:

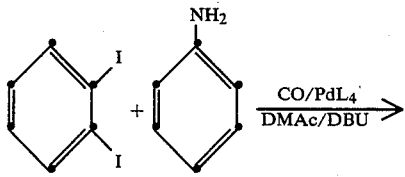

(1)

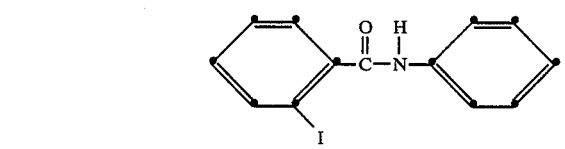

(2)

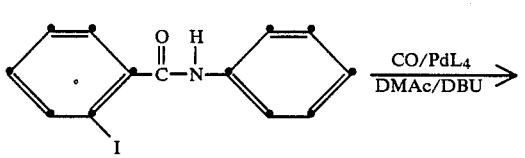

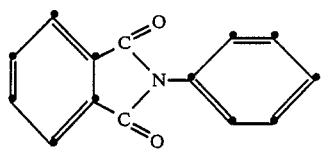

Although not bound by any theory, it is believed that the reactions depicted by Equations (1) and (2) may both proceed through an unisolated intermediate, formed by insertion of

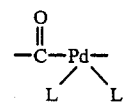

between the ring and the halide radical. Thus, for example, it is believed that the intermediate formed in Equation (2) has the formula:

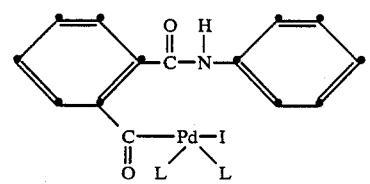

where L is a ligand such as triphenylphosphine. The above process suggests that it is not necessary to use an aromatic orthodihalide reactant (i.e., an aryl compound with 1,2-dihalofunctionality) as depicted in the above example. More specifically, it suggests that one may use a cis-1,2-dihalovinyl compound, and react it with CO and a primary amine as illustrated by the following unbalanced, simplified equation:

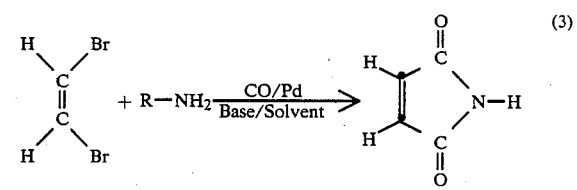

(3)

If the starting halo compound has a pair of halogen radicals as illustrated above plus another isolated halogen, i.e., a halogen not on a carbon atom adjacent to a halogen-substituted carbon, the product will have amide and imide groups, as illustrated by the following, where Y is a linking bond or a bridging group.

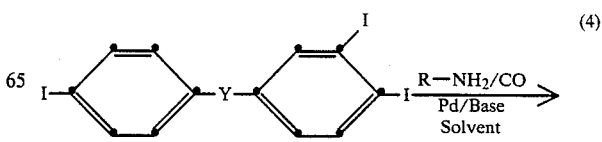

(4)

-continued

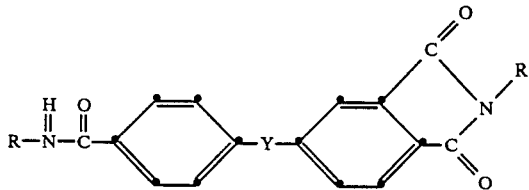

Oligomeric or polymeric products can be produced by reactions similar to the above; for example, by reacting carbon monoxide with a compound having two primary amine groups and a compound having two pair of halogen atoms. Similarly, oligomers or polymers can be made by polymerizing a compound having an amino group and a pair of adjacent, aromatic, or vinylic halogens in the presence of CO, palladium catalyst, base, and solvent.

The monomeric, oligomeric, and polymeric compounds can be used as chemical intermediates. The oligomeric and polymeric imides have the utilities known for these classes of materials. For example, the polyimides can be used as engineering plastics.

It will be noted from the above equations that the process of this invention for preparing polyimides does not employ reactants commonly used in the art for preparing such materials. Some of the prior art reactants, e.g., anhydrides are susceptible to hydrolysis. The reactants used in the present process are not. Furthermore, it will also be noted that water is not formed as a by-product in the instant process. Hence, the process of this invention has inherent advantages over known, prior processes for polyimide formation.

DESCRIPTION OF PREFERRED EMBODIMENTS

This invention comprises embodiment (1) a process for the preparation of a cyclic imide, said process comprising reacting carbon monoxide and a primary amine with a vicinal organo dihalide, i.e., a dihalide which has two halogen radicals (selected from bromide and iodide) on adjacent carbon atoms, said dihalide selected from the class consisting of aryl ortho dihalides and cis-1,2-dihalovinyl compounds; said process being conducted in the presence of a catalytic quantity of a palladium catalyst, an ether or dipolar aprotic solvent, and a base for neutralizing by-product hydrogen halide.

This invention also comprises embodiment (2) a process for the preparation of an acyclic monomeric imide, said process comprising reacting an aryl or vinyl mono-iodide or mono-bromide with a primary or secondary amide and carbon monoxide; said process being conducted in the presence of a catalytic quantity of a palladium catalyst, a dipolar aprotic solvent, and a base for neutralizing by-product hydrogen halide.

This invention also provides embodiment (3) which comprises five processes for the formation of an oligomeric or polymeric product having imide and/or amide groups. Such materials can be prepared by reacting carbon monoxide:

(3a) with an organic compound containing two halo functions, each of which are independently selected from the aryl monohalide and vinyl monohalide functions described in (2) above, e.g., 1,4-diiodobenzene, and with a primary amine such as aniline, to form an oligomeric or polymeric acyclic imide having Formula I below:

(3b) with an organic compound containing two dihalo functions, each of which is independently selected from the ortho dihalide and cis-1,2-dihalovinyl functionalities described in embodiment (1) above, and with a primary diamine, to form an oligomeric or polymeric cyclic imide having Formula II below;

(3c) with an organic compound having a dihalo function as described in (3b) above and also having a monohalide function as described in (3a), said monohalide being isolated from the dihalo function, and with a primary diamine, to form a cyclic imide/amide oligomer or polymer having Formula III below;

(3d) with an organic compound containing two dihalo functions, each being independently selected from the aryl ortho dihalide and cis-1,2-dihalovinyl functions described above, and with a primary or secondary diamide, to prepare an oligomeric or polymeric acyclic imide having Formula IV below; and (3e) with an organic compound having two isolated monohalide functions selected from aryl halides and vinyl halides of the type described in (2) above, and with a reactant having both (i) a primary or secondary amino groups, and (ii) a primary or secondary amido group, to produce an acyclic imide-amide oligomer or polymer having Formula V below. Each of reactions (3a)–(3e) is conducted in the presence of a catalyst, solvent, and base as mentioned above.

As indicated above, the preferred processes for preparing oligomers and polymers employ difunctional starting materials. Products made from such starting materials are generally linear and tractable. If one or more of the reactants are trifunctional, non-linear products can be formed. Such products generally are less tractable, i.e., less capable of producing useful end products. Hence, in many instances, processes of this invention which utilize trifunctional starting materials are less preferred.

Method (1) provides monomeric cyclic imides if one of the reactants, either the aromatic halide or the primary amine, is monofunctional, i.e., has only one functional group to react according to the process of this invention. Similar considerations hold for method (2).

Oligomers and polymers made by processes (3a)–(3e) inclusive are described below:

Acyclic imide oligomers and polymers of this invention have the formula

$n > 1$ wherein R is the moiety from the primary amine reactant and each R' is the moiety derived from a halide reactant having two halide radicals substituted on carbons which are not adjacent to one another.

Cyclic imide oligomers and polymers of this invention have the formula:

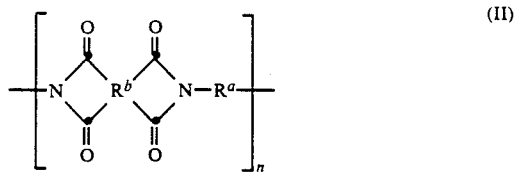

-continued n > 1 wherein $R^a$ is the moiety from the primary diamine reactant and $R^b$ is the moiety derived from the halide reactant having two pair of adjacent halide radicals.

Cyclic imide/amide oligomeric and polymeric products of this invention have the formula:

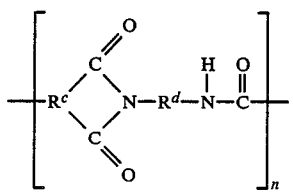 (III)

n > 1 wherein $R^c$ is the moiety from the halide reactant and $R^d$ is the moiety from the primary diamine reactant.

Acyclic imide oligomers and polymers of this invention have the formula:

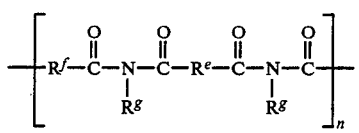 (IV)

n > 1 wherein $R^e$ is the moiety from the primary or secondary amide reactant, and each $R^f$ is the moiety derived from a halide reactant having two halide radicals substituted on carbons which are not adjacent to one another and $R^g$ is either an H radical or an organic radical such as a lower alkyl or lower aryl radical, i.e., a radical having up to about 10 carbon atoms.

Acyclic imide/amide oligomeric and polymeric products of this invention have the formula:

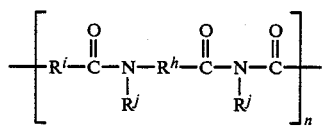 (V)

n > 1 wherein $R^h$ is the moiety from the primary or secondary amine/amide reactant, and $R^i$ is the moiety derived from a halide reactant having two halide radicals substituted on carbons which are not adjacent to one another and each $R^j$ is either an H radical, or an alkyl or aryl such as $R^g$ described above.

In the above formulas, n is an integer having a value of 2 to about 500 or higher, more preferably from 2 to about 350. For the purpose of this invention, when the value of n is from 2 to about 10, the products are referred to as "oligomers"; when the value of "n" is higher, the products are referred to as "polymers".

The reactants from which these products are derived are discussed and illustrated below.

Some aryl ortho dihalides useful in this invention as starting materials have the formula:

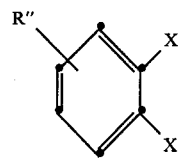

wherein each X is independently selected from bromine and iodine, and R″ is an inert substituent.

As set forth more fully below, the dihalide need not be a benzenoid compound as depicted above. Rather, it may be a dihalide derivative of a fused ring compound. Alternatively, the dihalide may have two or more aryl groups bonded together or linked by a linking group. The dihalides may have additional substitution.

For example, in a fused ring compound, or in a compound having two linked aryl groups, or two bridged aryl groups, there may be two pair of halogens ortho to each other. Reaction of such a compound with a compound having a plurality of primary amino groups according to this invention will yield a polymeric or oligomeric cyclic imide.

Moreover, a reactant employed in this invention may have a pair of halogens ortho to each other and one or more additional halogens which are "isolated", i.e., not vicinal, i.e., not ortho or adjacent to another halogen. Reaction of this type of compound, according to this invention, with a reactant having two or more primary amino groups will yield a polymeric or oligomeric material having imide and amide linkages.

The reactants of this invention may have a pair of ortho halogens and a primary amino substituent (—NH₂) in the molecule. When these materials are reacted with CO according to this invention, they can form a polymeric or oligomeric substance with imide groups.

From the above it can be seen that a wide variety of halides can be reacted according to this invention. They may be exemplified by compounds having one of the following general formulas wherein X is bromide or iodide and Y is carbon or a hetero atom such as, but not limited to, oxygen, nitrogen, sufur, phosphorous, silicon, etc.

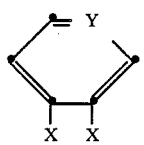

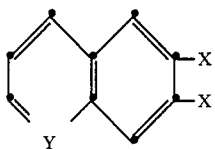

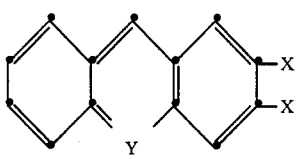

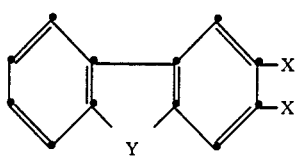

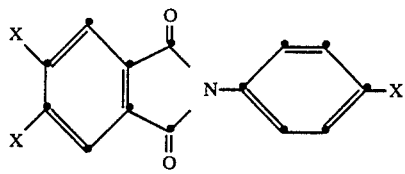

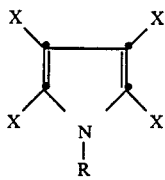

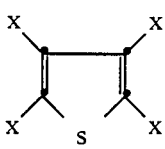

It will be apparent to a skilled practitioner that ortho dihalo derivatives of other fused ring systems are also applicable in this invention, and that the ortho halogen pair may be in positions other than illustrated above.

In addition, the pair of ortho halogens may be within compounds having two or more isolated aryl rings which are bonded together, such as ortho dihalo derivatives of biphenyl and terphenyl. Also, the pair of ortho halogens may be substituted on rings within compounds having two or more fused ring systems that are bonded together or that have a fused ring system bonded to a benzenoid nucleus as in the following examples:

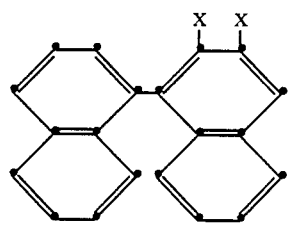

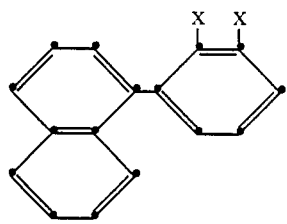

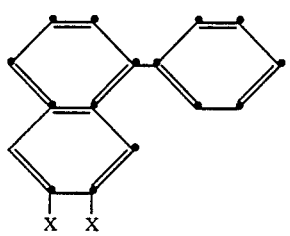

In accordance with the description above, additional reactants employed in this invention are exemplified by the following compounds:

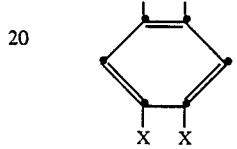

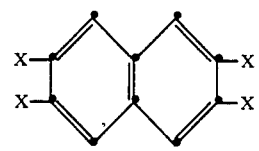

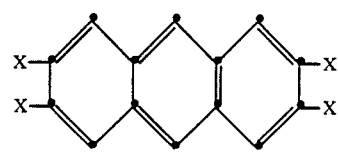

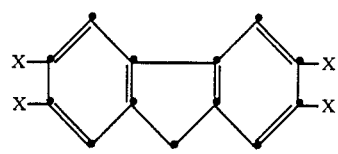

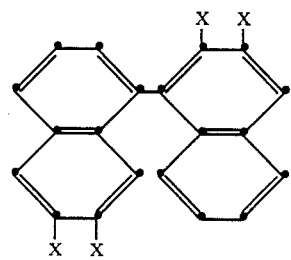

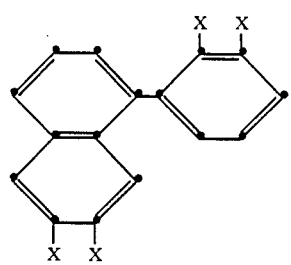

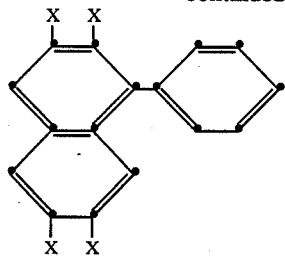

and also by compounds similar to the above wherein one of the ortho halogen pair is replaced with a single halogen.

Additional reactants useful in this invention are illustrated by:

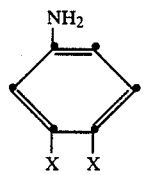

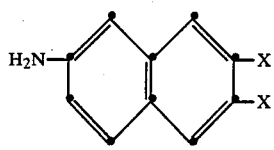

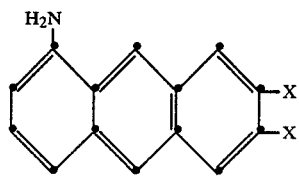

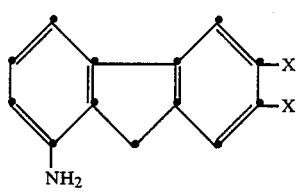

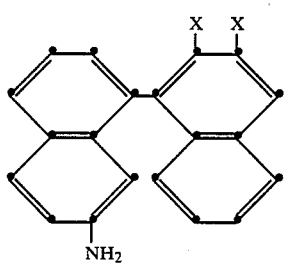

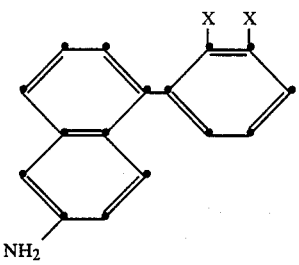

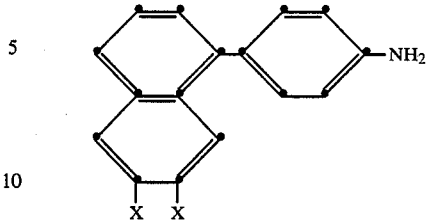

Reactants analogous to the above can have the rings or fused ring systems bridged by a bridging group rather than bonded together by a carbon-to-carbon bond. Typical bridging groups are:

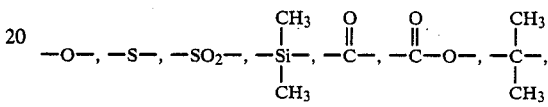

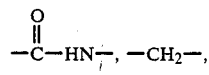

and —$CH_2$—$(CH_2)_n$—$CH_2$—, wherein n is from about 1 to about 6 or higher, and the like. Such reactants are illustrated by the following formulas, wherein Y' is a bridging group of the type illustrated above or phenylene, vinylene, carbonate, or

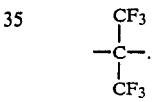

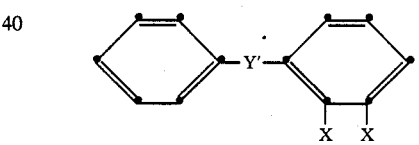

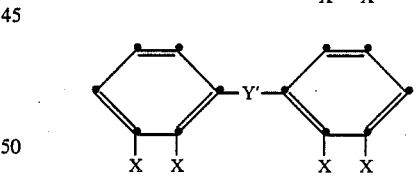

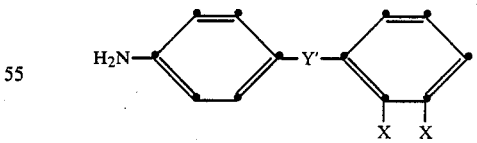

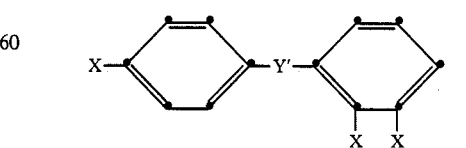

In addition, the bridging group Y' can bridge a benzene nucleus with a fused ring system, or two fused ring systems:

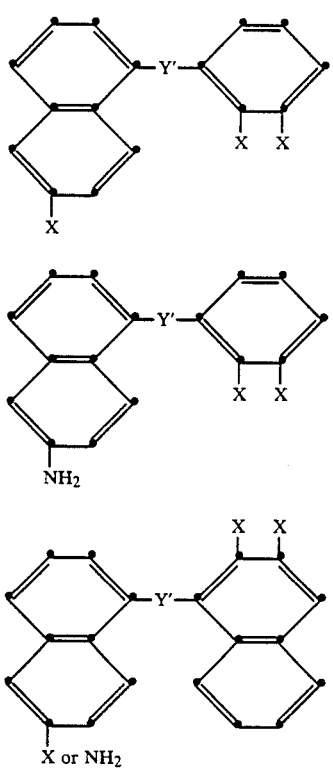

Other fused ring systems similar to those illustrated above can be linked by a bridging group Y', and substituted with a pair of ortho halogens, or two or more pair of ortho halogens, or one pair of ortho halogens and one ortho halogen or —NH₂ group.

Of the dihalo reactants mentioned above, it is preferred to use ortho diiodo aromatic compounds.

Preferred ortho diiodo aromatic compounds useful as reactants are illustrated by:

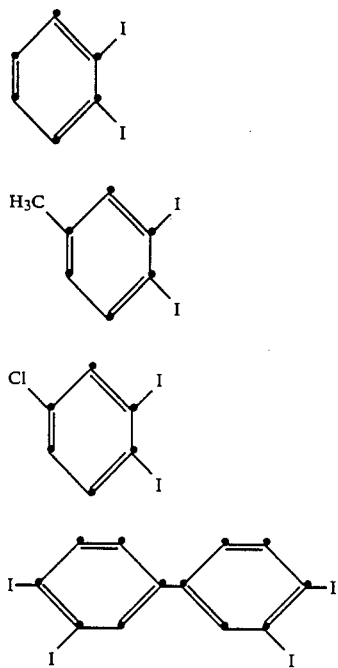

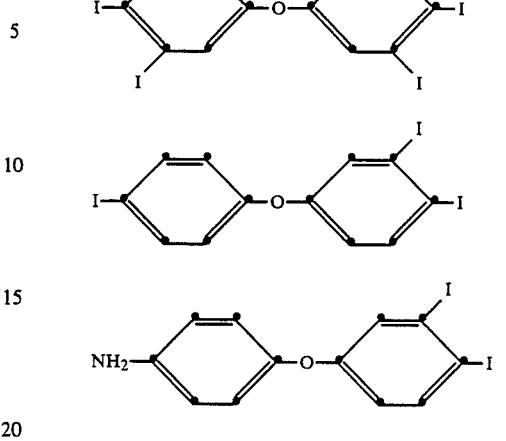

Cis-vinyl dihalides have been mentioned above as reactants in this invention. The vinyl linkage may be in a chain or ring, e.g., in cyclopentene. Two cyclopentene groups can be bonded together by a carbon-to-carbon bond, or linked by a bridging group. Alternatively, the cyclopentene ring can be a substituent on an aryl nucleus as in

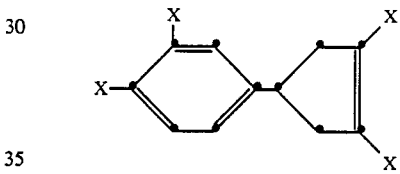

The cyclopentene ring can be substituted with an amino group —NH₂, or by an alkenyl radical having a vinyl bromide or iodide radical.

Preferably, the amine reactant is an alkyl or aromatic amine. It can be aniline, or alternatively be a primary or secondary amine derivative of one of the fused or bridged ring systems of the type illustrated above. Similarly, there may be two or more primary amino groups substituted on a benzenoid nucleus, or on a fused ring system or a bridged ring system.

Aliphatic primary amines can be used in this process. They may be saturated or unsaturated. They may also comprise one or more (non-aryl) rings or be acyclic. Preferably, the aliphatic amines are alkyl primary or secondary amines wherein the alkyl group or groups have up to about 10 carbon atoms. The alkyl groups may be branched or unbranched. Preferably the amines are liquids or solids that are soluble or dispersible in the reaction mixture.

Compounds having two or more primary amino groups within the molecule are illustrated by the following compounds:

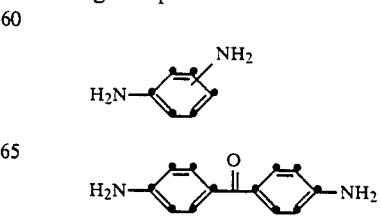

-continued

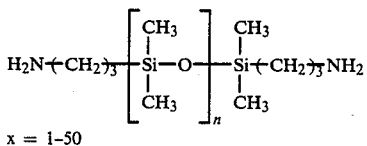

x = 1-50

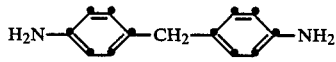

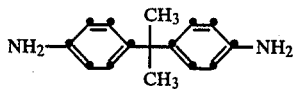

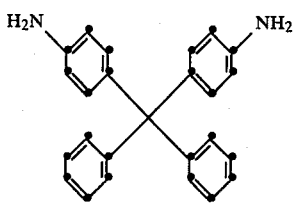

y = 1-10

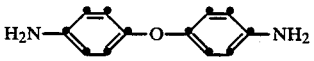

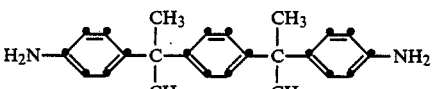

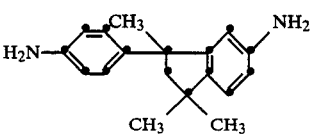

Amide and amide/amine reactants used in this invention are analogous to the amines described and illustrated above, i.e., there is a

i.e., carbonyl group inserted between the organic moiety and one or more of the —NH$_2$ or NHR function(s). Secondary amine and amide reactants useful in this invention have organic moieties attached to the

function which do not unduly inhibit the reaction by steric hindrance. Prferably, one of the organic moieties is an alkyl or aryl group having up to about 8 carbon atoms.

As can be seen by the above description, a wide variety of dihalo and amino reactants can be used in the processes of this invention. Preferably, such reactants are "stable" under the reaction conditions employed, i.e., they do not decompose to an unacceptable extent during the process of this invention. The organic materials used in this invention are also "suitable reactive", i.e., the process of this invention without entering into an unacceptable amount of undesirable side reaction(s). Thirdly, the organic reactants used in this invention be "sterically suitable", i.e., that they not be so bulky as to unduly retard the reaction by steric hindrance. Examples of such reactants have been given above.

The amine and halide reactions are contacted with carbon monoxide. The CO may be at atmospheric pressure or at a higher pressure. Carbon monoxide pressures in the range of from about 1 to about 200 atmospheres or higher can be used in the process.

Pressures lower than atmospheric can be used if desired, but generally do not confer any advantage.

The process proceeds well when the reactants are contacted in stoichiometric amounts. However, it is not necessary to use stoichiometric quantities. An excess of one or more reactants can be used to drive the reaction toward completion. A convenient amount of excess is preferably used. In other words, one employs an amount of excess which provides the desired result, but which does not unduly hinder the process by adding unacceptable cost, or by complicating the process by making it unduly difficult to separate product from unreacted materials.

It is convenient to add an excess of carbon monoxide to the reaction zone. The excess of CO need not be measured; one may merely pressurize the vessel with CO to the desired reaction pressure.

When one of the organic reactants is used in excess, it is preferably used in an amount of from 1.001 to about 5 times the molar amount required by stoichiometry.

The process of this invention is conducted in the presence of a liquid reaction medium to facilitate contacting the reactants. A wide variety of organic compounds can be used for this purpose so long as the reaction medium is "inert", i.e., does not enter into the reaction in an undesired way. It is preferred that the reaction medium dissolve the reactant(s) to an appreciable extent. For preparation of monomeric cyclic imides, an ether solvent can be used. A preferred solvent of this type is tetrahydrofuran or diglyme (2-methoxyethyl ether), or glyme (1,2-dimethoxy ethane). For preparation of oligomeric and polymeric products, a dipolar aprotic solvent is preferentially employed. Such solvents are characterized by the lack of acidic, easily abstractable hydrogens and a highly polar molecule. Typical dipolar aprotic solvents are dimethyl formamide, dimethylacetamide, dimethylsulfoxide, hexamethylphosphoramide, and the like.

The amount of liquid reaction medium is not critical. Generally, one uses enough medium to facilitate the reaction. There is no real upper limit on the amount of reaction medium employed. However, practical limits are imposed by the size of the reaction vessel, the ease of separation of product(s) from the reaction medium, cost, and similar considerations. Generally, the amount of liquid reaction medium employed is within the range of from about 0.1 to about 800 volumes based on the volume of halo or vinyl aromatic employed.

The process of this invention is conducted in the presence of a catalyst. The catalyst is preferentially a palladium compound, where palladium is present in the zerovalent or divalent state. Other transition metal catalysts, e.g., nickel and cobalt catalyst can be used. The palladium catalysts generally have one or more ligands bonded to the palladium atom(s) by ionic or covalent bonds. Simple palladium salts such as PdX$'_2$ wherein X' is Cl, Br, or I can be used. Other representative palladium catalysts are listed below:

TABLE I
Palladium Catalysts

| $Pd^{+2}$ | |
|---|---|
| $PdX_2$ | X = Cl, Br, I |
| $PdX_2L_2$ | X = Cl, Br, I |
| | L = $R_3P$, where R = alkyl or aryl |
| $Pd(OAc)_2$ | OAc = acetate |
| $Pd(OAc)_2L_2$ | OAc = acetate |
| $PdCl_2(RCN)_2$ | R = $CH_3$, Phenyl |
| $PhPdXL_2$ | X = Br, I |
| $PdCl_2(COD)_2$ | COD = cis,cis-1,5-cyclooctadiene |
| $Pd(acac)_2$ | acac = 2,4-pentanedionate |
| $Pd(o)$ | |
| $PdL_4$ | |
| L = $R_3P$ where | |
| R = alkyl or aryl | |

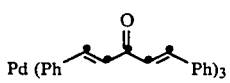

A catalytic amount of catalyst is employed. By "catalytic amount" is meant an amount of catalyst which catalyzes the reaction to the desired extent. Generally, the amount of catalyst is at least about 0.05 mole percent based on the amount of aryl or vinyl halide. There is no real upper limit on the amount of catalyst, this being defined by secondary conditions such as cost and ease of separation of the catalyst from products and unreacted reactants. A preferred catalytic amount is from about 0.005 to about 0.20 moles per mole of aryl or vinyl halide, more preferably from about 0.02 to about 0.10 mole per mole of halide reactant.

The process of this invention is preferably conducted in the presence of a base to neutralize by-product hydrogen halide. The base may be a tertiary amine such as tributylamine, pyridine, 1,8-diazobicyclo[5,4,0]-7-undecene (DBU) or have the formula:

$N(R)_3$ wherein each R is independently selected from lower alkyl groups having from about 2 to about 6 carbon atoms. The base may be immobilized on a cross-linked polymer such as cross-linked poly(vinylpyridine) heads. Alternatively, the base may be another type of basic substance which does not react with the reactants, e.g., a metal carbonate such as $K_2CO_3$ or a metal hydroxide such as $Ca(OH)_2$. Generally, one employs at least enough base to react with the by-product HX produced. An excess can be used, if desired.

As with the reactants, solvents and catalysts, a skilled practitioner will recognize that the exact structure of the base is not critical, and the example of compounds set forth above are merely illustrative and not-limiting examples of materials that can be used in this invention. A skilled practitioner will recognize that other materials can be substituted in this invention to achieve similar results.

The process of this invention is preferably conducted at a temperature within the range of from about ambient to about 250° C. A preferred temperature range is from about 60° C. to about 160° C. A skilled practitioner will recognize that the reaction temperature is not critical, and that temperatures outside this range can be employed, if desired. Generally, one selects a reaction temperature which affords a reasonable rate of reaction and which does not given an undue amount of decomposition of products or reactants.

The reaction time is not a truly independent variable, but is dependent at least to some extent based on the other reaction parameters selected such as reactivity of the reactants, activity, and amount of catalyst, reaction temperature, pressure, and similar variables. Generally speaking, reaction times within the range of from about 0.1 to about 100 hours are used.

EXAMPLE 1

Preparation of N-phenylphthalimide

To a dry 3-neck, 25 mL round bottom flask equipped with a Teflon ® resin coated stir bar, a balloon filled with carbon monoxide and a vacuum/argon inlet was placed o-diiodobenzene (320 mg, 0.97 mmol), aniline (90 mg, 0.97 mmol), palladium tetrakis(triphenylphosphine) ($PdL_4$) (56 mg, 0.048 mmol=5%) and N,N-dimethylacetamide (DMAc, 2.9 mL). The mixture was stirred and degassed three times with argon, and then the argon atmosphere was replaced with carbon monoxide by three successive evacuations of the flask. The flask was then immersed in a 115° C. oil bath and heated until the reagents had dissolved. Then 1,8-diazobicyclo[5,4,0]undec-7-ene (DBU, 320 μl, 2.13 mmol) was added by syringe. After about 12 hours the product was produced in quantitative yield as determined by gas chromatography. The mixture was cooled, diluted with chloroform, extracted with water, dried over $MgSO_4$, precipitated with methanol, collected by filtration, and dried in vacuo to give 40 mg product (19%). Much of the product remained in the filtrate.

The preparation of N-phenylphthalimide described above can be improved by increasing the carbon monoxide pressure from one atmosphere to 90 psi. Thus, to a dry 60 mL Fisher-Porter ® bottle equipped with a Teflon coated stir bar and a head fitted with a pressure gauge, a syringe inlet, a gas inlet, and a pressure release valve was added α-diiodobenzene (200 μl, 1.53 mmol), aniline (140 μl, 1.53 mmol), $PdCl_2L_2$ (65 mg, 0.092 mmol, 6%), triphenyl phosphine (49 mg, 0.184 mmol), and DMAc (7.7 mL). The contents of the bottle were degassed and placed under one atmosphere of carbon monoxide and heated to 115° C. in an oil bath. When the contents of the bottle had dissolved, DBU (550 μl, 3.69 mmol) was added by syringe and the bottle charged to 90 psi with carbon monoxide. After two hours, the product was produced in quantitative yield as determined by GC as compared to 12 hours under one atmosphere.

The preparation of N-phenylphthalimide can also be improved by increasing the temperature from 115° C. to 150° C. Thus, at 90 psi, 6% $PdCl_2L_2$ and 150° C., quantitative product formation occurs in 45 minutes rather than 2 hours at 115° C.

The catalyst $PdL_4$ can be replaced with chloride ($PdCl_2L_2$) by adding two equivalents of triphenyl phosphine.

EXAMPLE 2

Preparation of N-phenylphthalimide

A flask equipped as in Example 1 was charged with o-dibromobenzene (270 mg, 1.14 mmol), aniline (106 mg, 1.14 mmol), $PdL_4$ (66 mg, 0.057 mmol=5%) and DMAc (3.5 mL). When the contents had dissolved, DBU (380 μl, 2.52 mmol) was added and the reaction was monitored by gas chromatography (GC). After 72 hours at 115° C. approximately 80% product had been formed as determined by GC.

EXAMPLE 3

Preparation of N-hexylphthalimide

A flask equipped as in Example 1 was charged with o-diiodobenzene (360 mg, 1.76 mmol), n-hexylamine (179° mg, 1.76 mmol), $PdL_4$ (126 mg, 0.109 mmol=6.2%) and DMAc (4 mL). Then DBU (633 μl, 4.23 mmol) was added. The reaction was allowed to proceed at 115° C. for 19.5 hours at which time there was no more starting iodide or amine as seen by GC. Isolation by dilution with chloroform, extraction with water, drying with $MgSO_4$, concentration and standing gave a crystalline solid which was washed with hexane to give 75 mg product (16%).

EXAMPLE 4

Preparation of N-methyl-N-benzoylbenzamide

A pressure vessel (Fisher-Porter bottle) equipped with a Teflon coated stir bar, a gas inlet, a pressure gauge, and a pressure release valve was charged with N-methylbenzamide (242 mg, 1.79 mmol), iodobenzene (200 μl, 1.29 mmol), $PdCl_2L_2$ (76 mg, 0.107 mmol), triphenylphosphine (56 mg, 0.214 mmol) and DMAc (3.4 ml) and heated (115° C.) under one atmosphere of CO until the reactants had dissolved. DBU (320 μl, 2.14 mmol) was then introduced into the reaction mixture and the reactor charged to 40 psi with CO. After 23 hours, the reactor was cooled to room temperature, depressurized, and the reaction mixture diluted (50 ml) with ether and extracted (3×50 ml) with water. The ether layer was dried over $MgSO_4$ and concentrated to give a red oil which was chromatographed on silica gel (2:1, hexane:ethyl acetate) to give 30 mg product (7%).

Example 4 illustrates the preparation of an acyclic imide using a preformed amide as a starting material. The process of the above example can be extended to use of a primary amide as a reactant. Suitable preformed amide reactants can be prepared by reacting a primary or secondary amine with an aryl iodide, as known in the art. Also, amides with imide functionality can be made according to the method of this invention described above.

Oligomeric and polymeric materials can be made by following the teachings of the above examples, and substituting for the reactants used in the examples, compounds which are polyfunctional, e.g., primary diamines, and aromatic and vinyl halides having at least two 1,2-dibromo or diiodo functionalities, of the type described and illustrated above. Generally speaking, polymeric products are produced instead of oligomers when the starting materials are more reactive, the reaction temperatures are higher, or the reaction is conducted for a longer time.

In the process of the above examples, the dimethyl acetamide solvent can be substituted with an ether such as those named above, or by N,N-dimethyl formamide, hexamethylphosphoramide, dimethylsulfoxide, 1,3-dimethyl-2-imidazoline, pyridine, and the like.

The DBU can be substituted with $K_2CO_3$, $Ca(OH)_2$, tri-butyl amine, pyridine, and the like.

The process can be conducted using $PdX_2$, $PdXL_2$, $Pd(OAc)_2$, $Pd(OAc)_2L_2$, $PdCl_2(C_6H_5CN)_2$, $PhPdXL_2$, $PdCl_2(COD)_2$, $Pd(acac)_2$, or $PdL_4$, and the like in an amount of from about 0.005 to about 0.20 per mole of halide.

A skilled practitioner familiar with the above-detailed description of the invention can make many modifications and substitutions without departing from the scope and spirit of the appended claims.

We claim:

1. Process for the preparation of acyclic monomeric imide, said process comprising reacting CO, iodobenzene, and an aryl primary amide wherein the aryl radical has from 6 to about 20 carbon atoms, said process being conducted in the presence of a catalytic quantity of a palladium catalyst, a solvent, and a tertiary amine to neutralize by-product hydrogen iodide;

said solvent being selected from ethers and dipolar aprotic solvents; said process being conducted at a temperature of from about ambient to about 250° C.

2. Process for the preparation of N-methyl-N-benzoylbenzamide, said process comprising reacting N-methylbenzamide, iodobenzene, and CO in the presence of a catalytic quantity of a palladium catalyst, a solvent, and a tertiary amine to neutralize by-product hydrogen iodide;

said solvent being selected from ethers and dipolar aprotic solvents; said process being conducted at a temperature of from about ambient to about 250° C.

* * * * *